United States Patent
Kim et al.

(10) Patent No.: US 11,710,565 B2
(45) Date of Patent: Jul. 25, 2023

(54) METHOD OF DETECTING FETAL CHROMOSOMAL ANEUPLOIDY

(71) Applicant: THERAGEN GENOMECARE CO., LTD, Suwon-si (KR)

(72) Inventors: Sun Shin Kim, Yongin-si (KR); Myung Jun Jeong, Suwon-si (KR); Kyung Tae Min, Suwon-si (KR); Min Ae An, Yongin-si (KR); Jung Su Ha, Suwon-si (KR); So Ra Lee, Suwon-si (KR); Jin Han Bae, Suwon-si (KR); Hee Jae Joo, Yongin-si (KR)

(73) Assignee: THERAGEN GENOMECARE CO., LTD., Suwon-si (KR)

( * ) Notice: Subject to any disclaimer, the term of this patent is extended or adjusted under 35 U.S.C. 154(b) by 1334 days.

(21) Appl. No.: 16/071,883

(22) PCT Filed: Jan. 9, 2017

(86) PCT No.: PCT/KR2017/000266
§ 371 (c)(1),
(2) Date: Jul. 20, 2018

(87) PCT Pub. No.: WO2017/131359
PCT Pub. Date: Aug. 3, 2017

(65) Prior Publication Data
US 2019/0103187 A1    Apr. 4, 2019

(30) Foreign Application Priority Data
Jan. 25, 2016   (KR) .................. 10-2016-0008903

(51) Int. Cl.
| | | |
|---|---|---|
| *G16H 50/20* | (2018.01) | |
| *G16B 20/00* | (2019.01) | |
| *G16B 30/00* | (2019.01) | |
| *G16B 20/10* | (2019.01) | |
| *G16B 40/20* | (2019.01) | |
| *G16B 20/20* | (2019.01) | |
| *G16H 50/30* | (2018.01) | |
| *G16B 40/00* | (2019.01) | |
| *G16B 50/00* | (2019.01) | |
| *C12Q 1/6806* | (2018.01) | |
| *C12Q 1/6827* | (2018.01) | |
| *G06F 17/18* | (2006.01) | |

(52) U.S. Cl.
CPC ........... *G16H 50/20* (2018.01); *C12Q 1/6806* (2013.01); *C12Q 1/6827* (2013.01); *G06F 17/18* (2013.01); *G16B 20/00* (2019.02); *G16B 20/10* (2019.02); *G16B 20/20* (2019.02); *G16B 30/00* (2019.02); *G16B 40/00* (2019.02); *G16B 40/20* (2019.02); *G16B 50/00* (2019.02); *G16H 50/30* (2018.01)

(58) Field of Classification Search
CPC ........ G16H 50/20; G16H 50/30; G16B 20/20; G16B 40/00; G16B 20/00; G16B 20/10; G16B 40/20; G16B 30/00; G16B 50/00; C12Q 1/6806; C12Q 1/6827; G06F 17/18
See application file for complete search history.

(56) References Cited

U.S. PATENT DOCUMENTS

2014/0235474 A1* 8/2014 Tang ................... C12Q 1/6869
702/19

FOREIGN PATENT DOCUMENTS

KR    10-2014-0108177    9/2014

OTHER PUBLICATIONS

Liao et al., Noninvasive Prenatal Diagnosis of Common Aneuploidies by Semiconductor Sequencing; Crossmark, PNAS May 20, 2014, pp. 7415-7420; vol. 111; No. 20.
Zhang et al., Statistical Approach to Decreasing the Error Rate of Noninvasive Prenatal Aneuploid Detction Caused By Maternal Copy Number Variation; Scientific Reports Nov. 4, 2015; pp. 1-9.
Yeang et al., Genome-Wide Normalized Score: a Novel Algorithm to Detect Fetal Trisomy 21 During Non-Invasive Prenatal Testing; Ultrasound Obstet Gynecol 2014; 44: 25-30; Jun. 12, 2014 In Wiley Online Library (wileyonlinelibrary.com).
Bayindir et al.; Noninvasive Prenatal Testing Using a Novel Analysis Pipeline to Screen for All Autosomal Fetal Aneuploidies Improves Pregnancy Management; European Journal of Human Genetics; 2015, vol. 23, pp. 1286-1293; Macmillian Publishers Limited.
Jensen et al.; High-Throughput Massively Parallel Sequencing for Fetal Aneuploidy Detection From Maternal Plasma; PLOS ONE; Mar. 2013, pp. 1-8; vol. 8; Issue 3; www.plosone.org.
Kim et al.; An Adaptive Detection Method for Fetal Chromosomal Aneuploidy Using Cell-Free DNA From 447 Korean Women; BMC Medical Genomics; 2016; pp. 1-8, vol. 9:61.

* cited by examiner

*Primary Examiner* — Jerry Lin
(74) *Attorney, Agent, or Firm* — Procopio, Cory, Hargreaves & Savitch LLP

(57) ABSTRACT

Provided are a method of detecting chromosomal aneuploidy of a targeted fetal chromosome, and a computer-readable medium having recorded thereon a program to be applied to performing the method. According to the present disclosure, fetal chromosomal aneuploidy may be non-invasively and prenatally diagnosed with excellent sensitivity and specificity.

16 Claims, 22 Drawing Sheets

(a)

(b)

(c)

(d)

METHOD OF DETECTING FETAL CHROMOSOMAL ANEUPLOIDY

TECHNICAL FIELD

The present disclosure relates to a method of detecting fetal chromosomal aneuploidy in a biological sample derived from a pregnant woman, and a medium related thereto.

BACKGROUND ART

Prenatal diagnosis refers to diagnosis of the presence or absence of diseases in a fetus before the fetus is born. Prenatal diagnosis is largely classified into invasive diagnostic methods and non-invasive diagnostic methods. Invasive diagnostic methods include, for example, chorionic villus sampling, amniocentesis, umbilical cord, etc. Invasive diagnostic methods may cause abortion, diseases, or malformations by impacting a fetus during the examination process, and therefore, non-invasive diagnostic methods have been developed.

Recently, it has been demonstrated that non-invasive diagnosis of fetal chromosomal aneuploidy is feasible by massively parallel sequencing of DNA molecules in the plasma of pregnant women. Fetal DNA is detectable in maternal plasma and serum from the seventh week of gestation, and the amount of fetal DNA in maternal blood increases as pregnancy progresses. When massively parallel sequencing of fetal DNA is carried out, a threshold for discriminating between euploid fetuses and chromosomal aneuploid fetuses is ambiguous, and thus there is a problem in that sensitivity and specificity for chromosomal aneuploidy detection are low.

Accordingly, it is necessary to develop a method capable of increasing sensitivity and specificity for chromosomal aneuploidy detection by clearly discriminating between euploid fetuses and chromosomal aneuploid fetuses.

DESCRIPTION OF EMBODIMENTS

Technical Problem

Provided is a method of detecting chromosomal aneuploidy of a target fetal chromosome.

Provided is a computer-readable medium having recorded thereon a program to be applied to performing the method of detecting chromosomal aneuploidy of a target fetal chromosome.

Solution to Problem

According to an aspect of the present disclosure, provided is a method of detecting chromosomal aneuploidy of a target fetal chromosome, the method including:

obtaining sequence information (reads) of a plurality of nucleic acid fragments obtained from a biological sample of a pregnant woman;

mapping the obtained reads to a reference human genome to assign the reads of the nucleic acid fragments to the chromosome;

calculating a GC content and a fraction of reads (Rf) of the nucleic acid fragments on the target chromosome to the number of the nucleic acid fragments, based on the reads of the nucleic acid fragments assigned to the chromosome;

selecting adaptive reference samples belonging to a shared range of unit values of Rf and unit values of GC content from reference samples, based on the calculated Rf and GC content on the target chromosome;

calculating z scores of a verification reference samples and z scores of the test samples using the selected adaptive reference samples; and determining that the target chromosome has chromosomal aneuploidy when, by comparing the calculated z scores of the verification reference samples with the z scores of the test samples, the z scores of the test samples are larger than the z scores of the verification reference samples.

The method includes obtaining reads of a plurality of nucleic acid fragments obtained from a biological sample of a pregnant woman.

The pregnant woman may be a pregnant woman carrying a single fetus or twin fetuses.

The biological sample may be blood, plasma, serum, urine, saliva, mucus, sputum, feces, tears, or a combination thereof. The biological sample may be, for example, plasma of the peripheral blood. The biological sample may include fetal nucleic acids. The fetal nucleic acids may be cell-free DNA (cfDNA). The fetal nucleic acids may be isolated DNA.

The obtaining of the reads of a plurality of nucleic acid fragments obtained from the biological sample of a pregnant woman may include isolating nucleic acids from the biological sample.

A method of isolating the nucleic acids from the biological sample may be performed by a method known to those skilled in the art. The isolated nucleic acid fragments may be about 10 bp (base pairs) to about 2000 bp, about 15 bp to about 1500 bp, about 20 bp to about 1000 bp, about 20 bp to about 500 bp, about 20 bp to about 200 bp, or about 20 bp to about 100 bp in length.

The obtaining of the sequence information of a plurality of nucleic acid fragments obtained from the biological sample of a pregnant woman may include performing massively parallel sequencing of the obtained nucleic acids.

The term "massively parallel sequencing" may be used interchangeably with next-generation sequencing (NGS) or second-generation sequencing. The massively parallel sequencing refers to a technique in which millions of nucleic acid fragments are sequenced simultaneously. The massively parallel sequencing may be performed in parallel by, for example, 454 platform (Roche), GS FLX titanium, Illumina MiSeq, Illumina HiSeq, Illumina Genome Analyzer, Solexa platform, SOLiD System (Applied Biosystems), Ion Proton (Life Technologies), Complete Genomics, Helicos Biosciences Heliscope, single molecule real-time sequencing technology (SMRT™) of Pacific Biosciences, or a combination thereof.

The method may further include preparing DNA libraries in order to perform the massively parallel sequencing.

The DNA libraries may be prepared according to procedures of the massive parallel sequencing. The DNA libraries may be prepared according to the instructions provided by a manufacturer of the massively parallel sequencing.

The obtained sequence information of the nucleic acid fragments may be also called reads.

The method includes mapping the obtained reads to a reference human genome to assign the reads of the nucleic acid fragments to the chromosome.

The reference human genome may be hg18 or hg19. The reads mapped to only one genome location in the reference human genome may be termed unique reads. Based on a unique sequence number, the reads of the nucleic acid fragments may be assigned to a chromosomal location. The chromosomal location may be within a consecutive region of a chromosome which is about 5 kb, about 10 kb, about 20 kb, about 50 kb, about 100 kb, about 1000 kb, or about 2000 kb in length. The chromosomal location may be on a single chromosome.

The method may further include excluding intervals with a low confidence level for reads from subjects of analysis by examining depth distribution of the reads of the nucleic acid fragments assigned to the chromosome at each interval, after assigning the reads of the nucleic acid fragments to the chromosome. The interval may be an interval which is set in units of about 5 kb to about 50 kb. For example, the interval may be an interval which is set in units of about 10 kb to about 40 kb, about 15 kb to about 30 kb, or about 20 kb to about 25 kb. By setting the intervals, GC content of the base sequence may be used to perform filtering. Further, by setting the intervals, grouping of the read depth and GC content of the nucleic acid fragments assigned to the chromosome may be performed and statistical analysis may be possible.

The excluding of intervals with a low confidence level for reads from subjects of analysis may include removing mismatches, removing multi-mapped reads, removing duplicated reads, or a combination thereof. To exclude intervals with a low confidence level for reads from subjects of analysis, quality filtering, trimming, perfect match, removal of multi-mapped reads, removal of PCR duplicated reads, or a combination thereof may be performed. The quality filtering may be a process of extracting high-quality reads with respect to quality of each base sequence obtained during a sequencing process. The trimming is a process of removing a poor-quality region because quality of the end of a base sequence is poor due to the nature of a sequencing device. For example, a nucleic acid fragment may be trimmed to a size of about 50 bp or more, more than about 50 bp, or more than about 100 bp. For example, a quality value of a nucleic acid fragment may be 20 or more, 30 or more, 40 or more, or 50 or more. The perfect match is a process of selecting only perfect matches when mapped to a reference human genome. Since multi-mapped reads are likely to be a repeated sequence region, the multi-mapped reads may be removed from the obtained reads. The removal of PCR duplicated reads is for removing more amplified regions due to errors during sequencing. Further, for statistical analysis, statistically significant results may be obtained by choosing groups with small deviation. Further, no depth region is usually the N-region of the chromosome, which may be removed from the subjects of analysis.

The method may further include performing locally weighted scatterplot smoothing (LOWESS or LOESS) regression analysis of the reads of the nucleic acid fragments according to the following Equation 1 to reduce GC content bias, after assigning the reads of the nucleic acid fragments to the chromosome:

$$Rf_{ij'}=RC_{ij}/\Sigma_{j=1}^{22}RC_{ij} \quad \text{(Equation 1).}$$

The GC content bias is also called GC bias. The GC bias refers to a difference between actual GC content of the sequenced reads and predicted GC content based on the reference sequence. The GC bias refers to the difference of the number of sequenced reads according to the change of GC content.

In Equation 1, $Rf_{ij'}$ represents a corrected fraction of reads on chromosome j in sample i, and $RC_{ij}$ represents a corrected number of unique reads on chromosome j in sample i.

The method may further include performing normalization of the reads of the nucleic acid fragments according to the following Equation 2, after assigning the reads of the nucleic acid fragments to the chromosome:

$$Rf_{ij'}=Rf_{ij'}/\Sigma_{i=1}^{N}Rf_{ij'} \quad \text{(Equation 2).}$$

In Equation 2, $Rf_{ij'}$ represents a normalized fraction of reads on chromosome j in sample i, and N represents the total number of samples.

The method may include calculating the GC content and fraction of reads (Rf) of the nucleic acid fragments on the target chromosome to the number of the nucleic acid fragments, based on the reads of the nucleic acid fragments assigned to the chromosome.

The fraction of reads (Rf) of the nucleic acid fragments is also called read ratio. The Rf represents a ratio of the nucleic acid fragments on the target chromosome to the total number of the nucleic acid fragments on every chromosome of a test sample.

The GC content represents a proportion (%) of guanine (G) and cytosine (C) in bases constituting DNA. The GC content may be calculated from Equation of GC content= (G+C)/(A+T+G+C).

The method may include selecting adaptive reference samples belonging to a shared range of unit values of Rf and unit values of GC content from reference samples, based on the calculated Rf and GC content on the target chromosome.

The reference sample may be obtained from a biological sample of a pregnant woman carrying one or more euploid fetuses. The method may further include establishing a linear regression model from all of the reference samples.

The term "adaptive" may be used interchangeably with the term "selective" or the term "personalized". The adaptive reference sample may be a reference sample adapted to a test sample, which is selected from all reference samples. The adaptive reference sample may be a reference sample belonging to Rf of the target chromosome±unit value, GC content of the target chromosome±unit value, or a shared range thereof, which is selected from reference samples. The unit value may be a value arbitrarily set, and the unit value of Rf and the unit value of GC content may the same as or different from each other. For example, the unit value (%) of Rf may be about 0.000001 to about 0.002, about 0.000005 to about 0.001, about 0.00001 to about 0.0005, or about 0.00005 to about 0.0001. The unit value (%) of GC content may be about 0.0001 to about 0.1, about 0.0005 to about 0.05, about 0.002 to about 0.02, or about 0.001 to about 0.01.

The method may further include extending the unit values of Rf of the reference samples according to Rf values of the test samples, extending the unit values of GC of the reference samples according to GC contents of the test samples, or a combination thereof. The extending of the unit values of Rf of the reference samples, the extending of the unit values of GC of the reference samples, or a combination thereof may be implemented by computer algorithms.

The method may include calculating z scores of a verification reference samples and z scores of the test samples using the selected adaptive reference samples.

The term "z score", one of standard scores, refers to a score calculated by dividing a score deviation by a standard deviation of the group. The z score allows relative comparison between scores with different means and units by converting the scores into a unit distribution with a mean of 0 and a standard deviation of 1.

The calculating of z scores of the verification reference samples and z scores of the test samples may include performing a linear regression analysis according to the following Equation 3 and calculating a linear predicted value of Rf according to the following Equation 4:

$$Rf_{ij'} = \alpha + \beta \times GC_{ij'} + e \quad \text{(Equation 3), and}$$

$$Rf'_{ij'} = \alpha + \beta \times GC_{ij'} \quad \text{(Equation 4).}$$

In Equation 3, $Rf_{ij'}$ represents a normalized fraction of reads on chromosome j in sample i, $\alpha$ represents a constant, $\beta$ represents a coefficient factor between GC content and Rf, and e represents a residual (R).

In Equation 4, $Rf'_{ij'}$ represents a fitted predicted value of fraction of reads on chromosome j in sample i, $\alpha$ represents a constant, and $\beta$ represents a coefficient factor between GC content and Rf.

The calculating of z scores of the verification reference samples and z scores of the test samples may include calculating a residual (R) from a calculated value from the linear regression analysis and the calculated linear predicted value according to the following Equation 5, and calculating a Z score from the calculated residual according to the following Equation 6:

$$R = Rf_{ij'} - Rf'_{ij'} \quad \text{(Equation 5); and}$$

$$z\ \text{score} = (R - R')/\sigma' \quad \text{(Equation 6).}$$

In Equation 6, R' represents a mean value of a residual of an adaptive reference sample, R represents a residual value of a test sample, and $\sigma'$ represents a standard deviation of the residual of the adaptive reference sample.

The method may include determining that the target chromosome has chromosomal aneuploidy, when, by comparing the calculated z score of the adaptive reference sample with the z score of the test sample, the z score of the test sample is larger than the z score of the adaptive reference sample.

The method may further include selecting reference samples belonging to GC content±unit value of the target chromosome as verification samples; calculating z scores of the verification samples; and verifying that the target chromosome has chromosomal aneuploidy by comparing the calculated z scores of the verification samples with the z scores of the test samples.

The method may further include determining that the target chromosome has chromosomal aneuploidy, when the calculated z score of the target chromosome of a test sample is more than 3.

The method provides a method of detecting chromosomal aneuploidy of a target fetal chromosome.

The target chromosome may be chromosome 13, chromosome 18, chromosome 21, an X chromosome, a Y chromosome, or a combination thereof.

The term "chromosomal aneuploidy" refers to a state in which the number of chromosomes per cell in cells, individuals, or lineages is not a multiple of the haploid number, a state in which one to several chromosomes are gained or lost with respect to euploidy, in other words, a state in which one chromosome set is incomplete. In the case of diploid, nullisomy refers to loss of both members of a homologous pair of chromosomes, monosomy refers to the absence of one chromosome and the presence of the other chromosome, and trisomy (T) refers to the presence of extra single chromosome in addition to a homologous pair of chromosomes.

The chromosomal aneuploidy may be trisomy 13, trisomy 18, trisomy 21, XO, XXX, XXY, XYY, or a combination thereof. Trisomy 13 is associated with Patau syndrome. Trisomy 18 is associated with Edwards syndrome. Trisomy 21 is associated with Down syndrome. Monosomy X (XO, e.g., loss of one X chromosome) is associated with Turner syndrome. XXY is the presence of an additional X chromosome in human males, and associated with Klinefelter syndrome.

According to another aspect, provided is a computer-readable medium having recorded thereon a program to be applied to performing the method according to one aspect. The computer-readable medium encompasses systems containing the computer-readable medium.

Advantageous Effects of Disclosure

According to a method of detecting chromosomal aneuploidy in a targeted fetal chromosome, and a computer-readable medium having recorded thereon a program to be applied to performing the method according to specific embodiments, fetal chromosomal aneuploidy may be non-invasively and prenatally diagnosed with excellent sensitivity and specificity.

MODE OF DISCLOSURE

Figure 1:
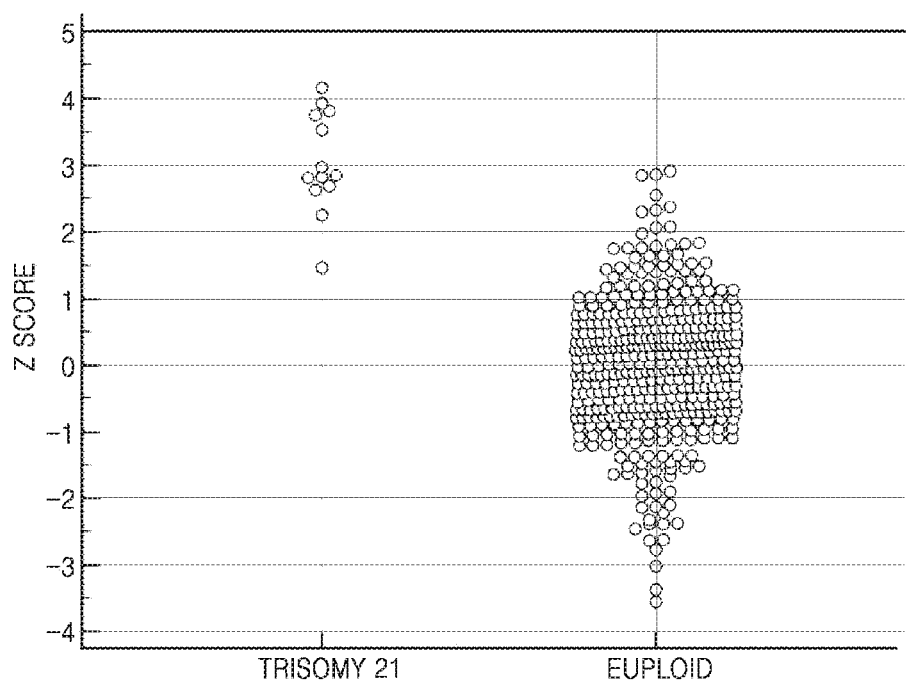
FIG. 1 is a graph showing, among all samples, z scores of euploid samples and trisomy 21 samples.
Figure 2:
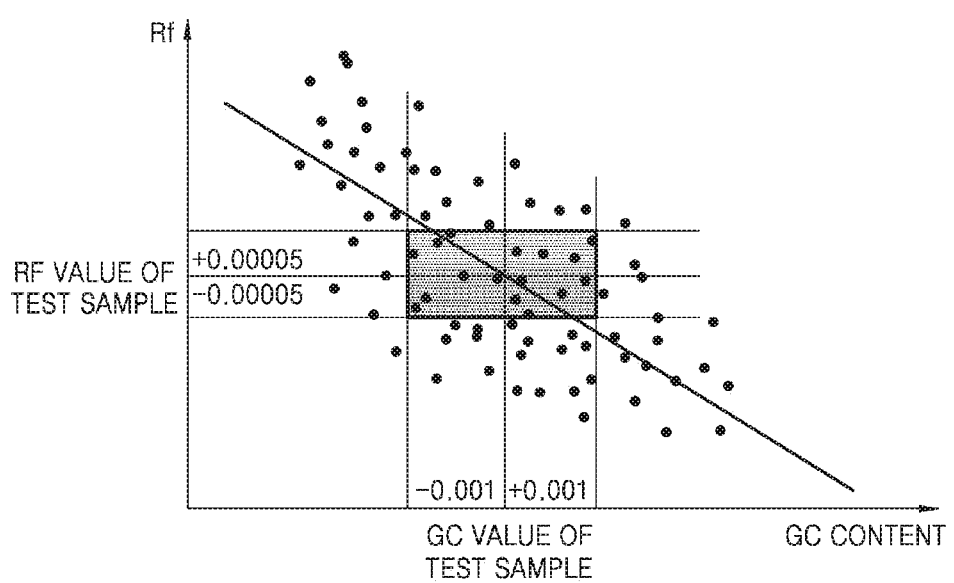
FIG. 2 is a graph showing selection of adaptive reference samples belonging to a shared range of fraction of reads (Rf) and GC content from among reference samples, based on Rf and GC content of a targeted chromosome, according to an embodiment.

Hereinafter, the present disclosure will be described in more detail with reference to Examples. However, these Examples are for illustrative purposes only, and the scope of the present disclosure is not intended to be limited by these Examples.

Example 1. Non-Invasive Detection of Fetal Chromosomal Aneuploidy

1. Preparation of Sample

A total of 447 pregnant women were enrolled at 12 hospitals in Korea. Information of the test subjects is shown in Table 1 below.

TABLE 1

| Characteristic | | Value |
| --- | --- | --- |
| No. of pregnant women | | 447 |
| Maternal age (year) | Mean | 35 |
| | Range | 20 to 46 |
| Gestational age (week) | Mean | 15 |
| | Median | 16 |
| | Range | 11 to 22 |
| Pregnancy trimester (%) | First: 1-13 week gestation | 137 (30.6) |
| | Second: 14-26 week gestation | 310 (69.4) |
| | Third: 27-40 week gestation | 0 |
| Fetal sex (%) | Male fetus | 249 (52.5) |
| | Female fetus | 225 (47.5) |

Of the test subjects, 29 were carrying twins, and information thereof is shown in Table 2 below.

TABLE 2

| Characteristic | | Value |
| --- | --- | --- |
| No. of pregnant women carrying twins | | 29 |
| Maternal age (year) | Mean | 35 |
| | Range | 22 to 43 |
| Gestational age (week) | Mean | 14 |
| | Median | 13 |
| | Range | 11 to 21 |
| Pregnancy trimester (%) | First: 1-13 week gestation | 16 (55.2) |
| | Second: 14-26 week gestation | 13 (44.8) |
| | Third: 27-40 week gestation | 0 |
| Fetal sex (%) | Male fetus | 26 (48.1) |
| | Female fetus | 28 (51.9) |

Two pregnant women with unknown fetal sex were excluded.

All 447 test subjects had amniocentesis for fetal karyotyping, the results of which were obtained by blind analysis. The institutional review board at each participating hospital approved this study. Written informed consent was obtained from all participants.

All test subjects underwent standard prenatal aneuploidy screening in accredited clinical laboratories. First-trimester screening includes measurement of serum pregnancy-associated plasma protein A (PAPP-A), total or free beta subunit of human chorionic gonadotropin (hCG), and nuchal translucency. Second-trimester screening includes measurement of maternal serum alpha-fetoprotein (MSAFP), hCG, unconjugated estriol, and inhibin A.

From the results of karyotyping, there were 13 fetuses with trisomy 21 (including three twin samples), one fetus with trisomy 18 in a twin pregnancy, one fetus with trisomy 13, and two fetuses with XXY. 17 samples with aneuploidy, 29 samples with twins, and 5 samples with higher GC contents were excluded from total 447 samples, and the remaining 396 samples were used as reference samples.

2. Preparation of Cell-Free DNA and DNA Libraries for DNA Sequencing

About 10 mL of peripheral blood was collected from each test subject described in 1. in a BCT™ tube (Streck, Omaha, Nebr., USA). Each of the collected blood samples was centrifuged at 1,200×g at 4° C. for 15 min. The plasma portion of blood was collected and centrifuged again at 16,000×g at 4° C. for 10 min. Cell-free DNA (cfDNA) was extracted from the centrifuged plasma by using a QIAamp circulating nucleic acid kit (Qiagen, Netherland).

The end-repair of the obtained cfDNA was carried out using T4 DNA polymerase, Klenow DNA polymerase, and T4 polynucleotide kinase, and then cfDNA fragments were obtained again by using Agencourt AMPure XP.

DNA libraries for ion proton sequencing systems were constructed from the prepared cfDNA according to the protocol provided by the manufacturer (Life Technologies, S. Dak., USA). Proton PI Chip Kit version 2.0 was used to yield an average 0.3× sequencing coverage depth per nucleotide.

3. Massively Parallel Sequencing

The DNA libraries prepared as in 2. were subjected to massively parallel sequencing by using ION PROTON™ system (Thermo Fisher Scientific).

Different raw reads were obtained using ION TORRENT SUITE™ software (Thermo Fisher Scientific). The number of the obtained raw reads was about $(7.4\pm2.1)\times10^6$ per sample on average.

The reads were trimmed from the 3' end by sequencing, and low-quality reads were excluded from the subjects of analysis. Further, the reads were filtered by a quality threshold value of 20 and a read length threshold of 50 bp.

The filtered reads were aligned to the human genomic reference sequences hg19 using Burrows-Wheeler transform (BWT). Sequence reads mapped to only one genome location in hg19 were termed unique reads. About 44.6% (about $3.3\times10^6$) of the total reads were unique reads. The GC contents of the total 447 samples ranged from about 30% to about 60%.

Meanwhile, duplicate DNA reads were removed from the subjects of analysis by Picard (http://picard.sourceforge.net/).

4. Correction and Normalization of DNA Reads

In order to reduce the effect of GC bias in the DNA reads obtained in 3., and difference between samples, correction and normalization of the DNA reads were performed.

First, all chromosomes were divided into segments with a bin size of 20 kb. The number of unique reads and GC content (rounded to 0.1%) in each bin were determined. Bins including reference sequences with undeterminable bases and bins without any reads were filtered.

Then, a locally weighted scatterplot smoothing (LOESS) regression analysis was used. In detail, the fit predicted value ($UR_{loess}$) of each bin was obtained by the number of unique reads (UR) in each bin against the GC content ($GC_{bin}$) of the corresponding bin according to the following equation: $UR_{loess}=f(GC_{bin})$. The LOESS-corrected reads number ($UR_{corrected}$) was calculated using the following equation: $UR_{corrected}=UR-[UR_{loess}-e(UR)]$, wherein $e(UR)$ was the expected value for unique reads of each bin, which was set to the overall average unique reads number in each bin (Liao C. et al., Proc. Natl. Acad. Sci., 2014, 111(20): 7415-7420).

After LOESS correction, a fraction of reads (Rf) of sample i on the chromosome j was calculated by the following equation:

$$Rf_{ij}=RC_{ij}/\Sigma_{j=1}^{22}RC_{ij} \quad \text{(Equation 1)}.$$

In Equation 1, $Rf_{ij}$, represents a corrected fraction of reads on chromosome j in sample i, and $RC_{ij}$ represents a corrected number of unique reads on chromosome j in sample i.

The normalized fraction of reads was calculated using the calculated $Rf_{ij}$, according to the following equation:

$$Rf_{ij'}=Rf_{ij'}/\Sigma_{i=1}^{N}Rf_{ij'} \quad \text{(Equation 2)}.$$

In Equation 2, $Rf_{ij'}$ represents a normalized fraction of reads on chromosome j in sample i, and N represents the total number of samples.

5. Selection of Adaptive Reference Sample and Detection of Fetal Aneuploidy (1) Calculation of Z Scores for all Samples and Detection of Fetal Aneuploidy Fetal aneuploidy was detected in all samples according to a previous method of calculating z score.

In detail, a full linear regression model for all samples was established, based on $Rf_{ij'}=\alpha+\beta \times GC_{ij'}+e$ (Equation 3). A fitted predicted value of fraction of reads was calculated by the following equation: $Rf'_{ij'}=\alpha+\beta \times GC_{ij'}$ (Equation 4). In the above Equations, $Rf_{ij'}$ represents a normalized fraction of reads on chromosome j in sample i, $Rf'_{ij'}$ represents a fitted predicted value of fraction of reads on chromosome j in sample i, represents a GC content on chromosome j in sample i, β represents a coefficient factor between a GC content and Rf, α represents a constant, and e represents a residual (R). The residual (R) was calculated according to $R=Rf_{ij'}-Rf'_{ij'}$ (Equation 5); Equation 5, and fitted to a normal distribution. The z score for fetal aneuploidy was calculated by the following equation: z score=$(R-R')/\sigma'$, wherein R represents a residual on the chromosome in the sample, R' represents the average value of the residuals in reference samples or test samples, and σ' represents the standard deviation of the residuals in reference samples or test samples. z score>3 represents a fraction of reads greater than that of the 99.9th percentile of the reference sample set.

Z scores of the euploid samples and trisomy 21 (T21) of all samples are shown in FIG. 1. As shown in FIG. 1, a z score range from about 1 to about 3 for chromosome 21 overlapped in the euploid samples and T21 samples, and positive and negative results were not clearly distinguished, and a threshold was ambiguous, indicating that the method of detecting fetal aneuploidy using z scores of the whole reference samples shows low accuracy and specificity.

(2) Detection of T21 Sample Using Adaptive Reference Sample

It was considered that the ambiguous threshold in the previous method of detecting fetal aneuploidy as described in 5.(1) could result from a suboptimal reference sample collection. Therefore, reference samples adapted to a test sample were selected from the whole reference samples, followed by statistical analysis.

First, GC contents of 13 positive samples (e.g., T21 sample) were examined. The positive samples were categorized into four groups according to GC content regions (ranging from −0.005 to +0.005). The two positive samples in the GC content region of 0.41, the five positive samples in the GC content region of 0.42, the two positive samples in the GC content region of 0.43, and the four positive samples in the GC content region of 0.44 were clustered according to the GC regions, respectively. Representative positive sample was selected from each group, and the selected positive sample was used to generate a set of adaptive reference samples by increasing the GC content by 0.001 and the reads fraction by 0.00005.

As adaptive reference samples, reference samples belonging to a shared range of the GC content and Rf were extracted from all reference samples. The GC content range was set from −0.001 to +0.001 as a unit value when setting the GC content of a test sample as the median. The Rf was set from −0.00005 to +0.00005 as a unit value when setting the Rf of a test sample as the median, which was determined by the fitting predicted fraction of Rf calculated as $Rf'_{ij'}=\alpha+\beta \times GC_{ij'}$ (Equation 4) from all reference samples.

A coefficient of variation (CV) was used to evaluate performance between the previous method of using whole reference samples and the method of using adaptive reference samples.

(i) Application of Adaptive Selection Method to T21 Test Samples in GC Content Region of 0.41

Figure 3A:
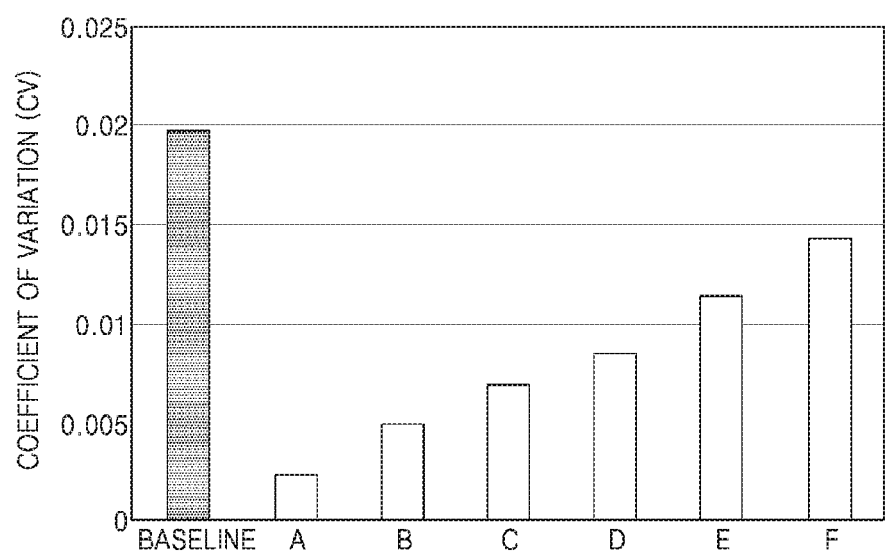
FIG. 3A shows coefficient of variation for six sets of reference samples which were selected according to a shared region of GC and Rf based on a representative sample of chromosome T21 with a GC content of 0.416.

The coefficient of variation for chromosome 21 was calculated with and without adaptive sample selection using reference samples selected from a shared region of GC content 0.416±X and Rf linear predicted value±Y. FIG. 3A shows coefficient of variation with and without adaptive reference selection.

In FIG. 3A, the baseline represents the coefficient of variation used to measure the genomic representation of chromosome 21 among reference samples (n=396) without adaptive reference selection. Of the two test samples in the GC content region of 0.41 of chromosome 21, one sample in the GC content region of 0.416 of chromosome T21 was selected as a representative test sample, and the other sample was used to verify results using the adaptive reference samples. Six sets of reference samples (A, B, C, D, E, and F) were selected according to shared ranges of GC content and Rf, based on the representative test samples (A: n=27, B: n=110, C: n=157, D: n=195, E: n=246, F: n=276), respectively. In FIG. 3A, CVs for the selected six sets of reference samples are shown. CVs for the selected sets, A to F were lower than CV of the baseline. Therefore, it was confirmed that the reference samples selected by adaptive selection may show uniform sample distribution and higher sensitivity and specificity for T21.

Figure 3B:
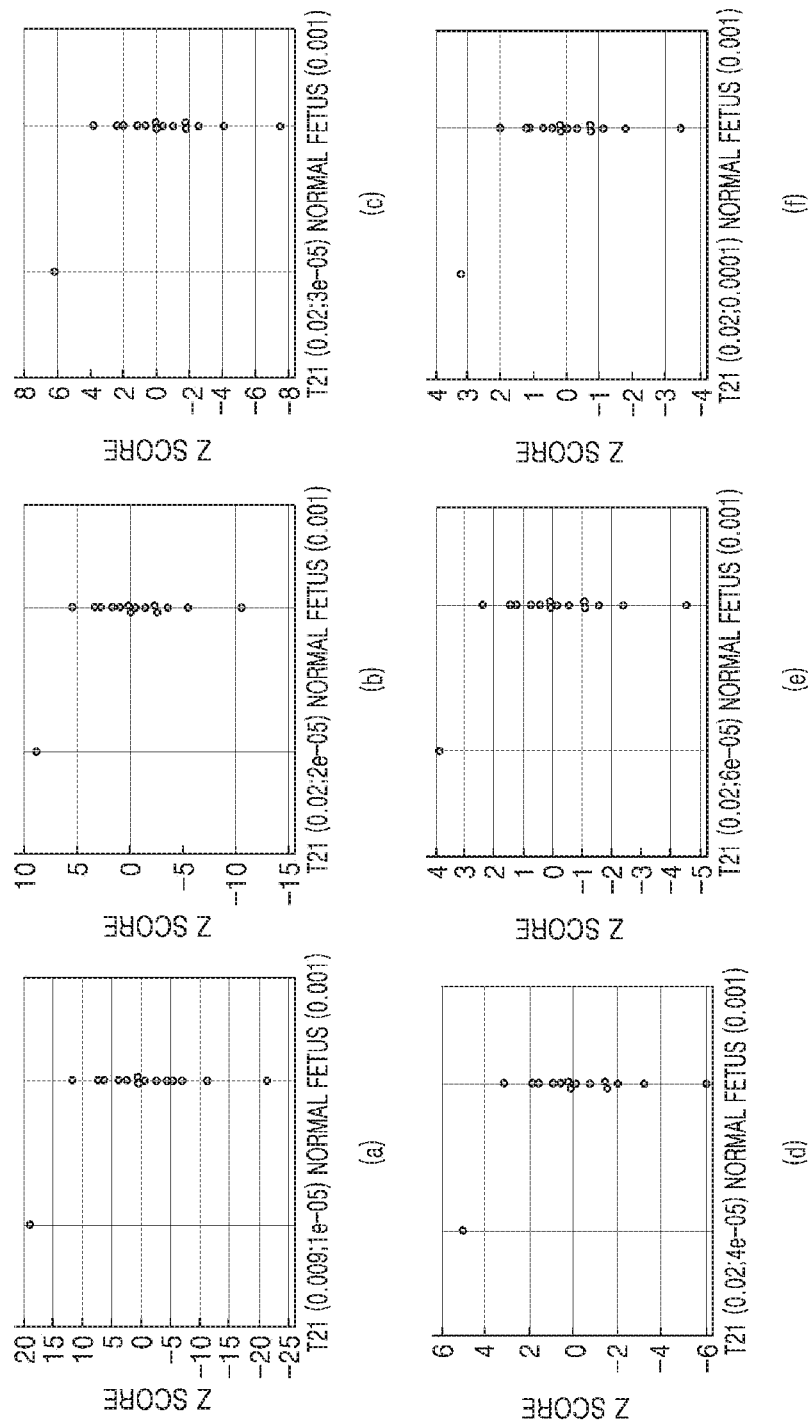
FIG. 3B shows results of calculating Z scores of T21 verification samples with a GC content of 0.41 and euploid verification samples using the euploid samples of sets A to F adaptively selected in FIG. 3A as reference samples.

(A) to (F) of FIG. 3B show results of calculating Z scores of T21 test samples and euploid test samples using the euploid samples of sets A to F adaptively selected in FIG. 3A as reference samples, and specifically, z scores of the euploid samples of adaptively selected sets A to F, and T21 test sample (n=1) in the GC content region of 0.41 (T21 (absolute value of GC content; absolute value of Rf), euploid (absolute value of GC content)). In (A), the reference samples corresponding to set A were selected from a shared range of GC content 0.416±0.009 and Rf linear predicted value±1e-05. In this regard, one remaining test sample not selected as the representative test sample was used as a verification sample. In (B) to (F), reference samples were selected in the same manner as in (A). z scores of the T21 test samples were calculated from the selected reference samples and test samples. Further, euploid samples arbitrarily selected in the GC content range of 0.416±0.001 were used as test samples, and the 6 sets of the reference samples were used to calculate z scores of the euploid test samples.

As shown in FIG. 3B, when the adaptively selected sets A to F were used, the euploid samples (normal fetus) and the T21 samples were clearly distinguished, and a threshold which is the z score for T21 was unambiguous.

(ii) Application of Adaptive Selection Method to T21 Test Samples in GC Content Region of 0.42

Figure 4A:
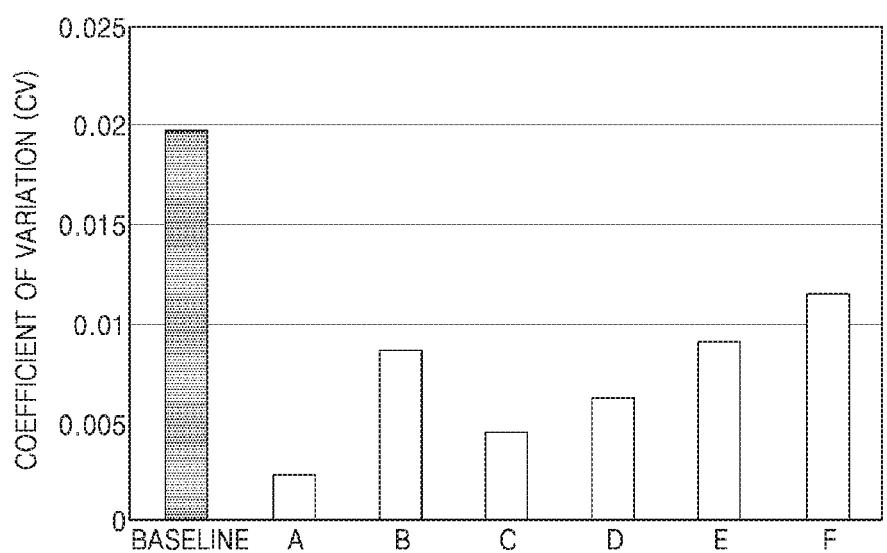
FIG. 4A shows coefficient of variation for six sets of reference samples which were selected according to a shared region of GC and Rf based on a representative sample of chromosome T21 with a GC content of 0.424.

Similarly, of the five test samples in the GC content region of 0.42 of chromosome 21, samples in the GC content region of 0.424 of chromosome T21 were selected as a representative test sample, and other samples were used to demonstrate results using the adaptive reference samples. Six sets of reference samples (A, B, C, D, E, and F) were selected according to shared ranges of GC content and Rf based on the representative test samples (A: n=37, B: n=210, C: n=120, D: n=166, E: n=226, F: n=278), respectively. In FIG. 4A, CVs for the selected six sets of reference samples are shown.

Figure 4B:
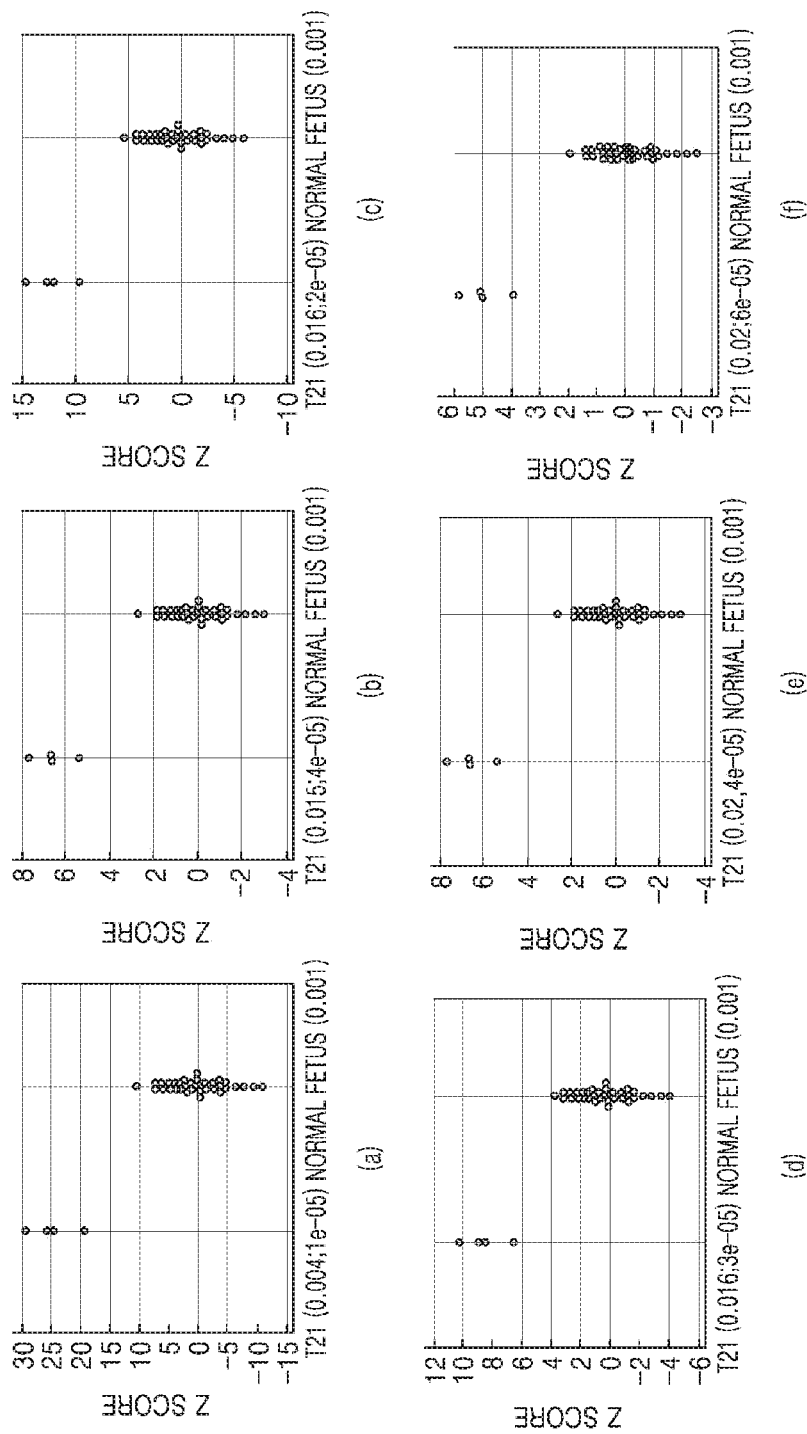
FIG. 4B shows results of calculating Z scores of T21 verification samples with a GC content of 0.42 and euploid verification samples using the euploid samples of sets A to F adaptively selected in FIG. 4A as reference samples.

(A) to (F) of FIG. 4B show results of calculating Z scores of T21 test samples and euploid test samples using the euploid samples of sets A to F adaptively selected in FIG. 4A as reference samples. In (A), the reference samples corresponding to set A were selected from a shared range of GC content 0.424±0.004 and Rf linear predicted value±1e-05. In this regard, the remaining test samples not selected as the representative test sample were used as verification samples. In (B) to (F), reference samples were selected in the same manner as in (A). z scores of the T21 test samples were calculated from the selected reference samples and test samples.

Further, euploid samples arbitrarily selected in the GC content range of 0.424±0.001 were used as test samples, and the 6 sets of the reference samples were used to calculate z scores of the euploid test samples. As shown in FIG. 4B, when the adaptively selected sets A to F were used, normal fetus (euploid) and T21 fetus were clearly distinguished, and a threshold which is the z score for T21 fetus was unambiguous.

(iii) Application of Adaptive Selection Method to T21 Test Samples in GC Content Region of 0.43

Figure 5A:
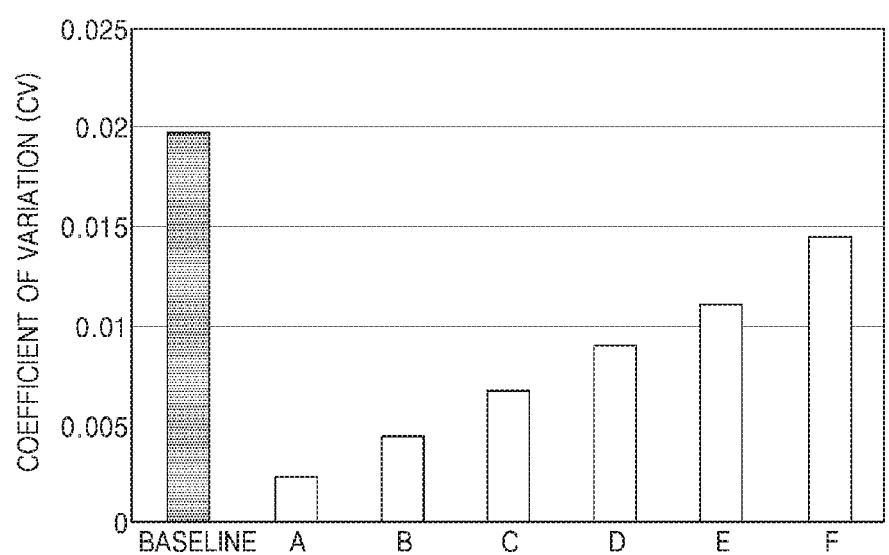
FIG. 5A shows coefficient of variation for six sets of reference samples which were selected according to a shared region of GC and Rf based on a representative sample of chromosome T21 with a GC content of 0.437.

Similarly, of the two test samples in the GC content region of 0.43 of chromosome 21, one sample in the GC content region of 0.437 of chromosome T21 was selected as a representative test sample, and the other sample was used to demonstrate results using the adaptive reference samples. Six sets of reference samples (A, B, C, D, E, and F) were selected according to shared ranges of GC content and Rf based on the representative test samples (A: n=31, B: n=90, C: n=138, D: n=189, E: n=227, F: n=292), respectively. In FIG. 5A, CVs for the selected six sets of reference samples are shown.

Figure 5B:
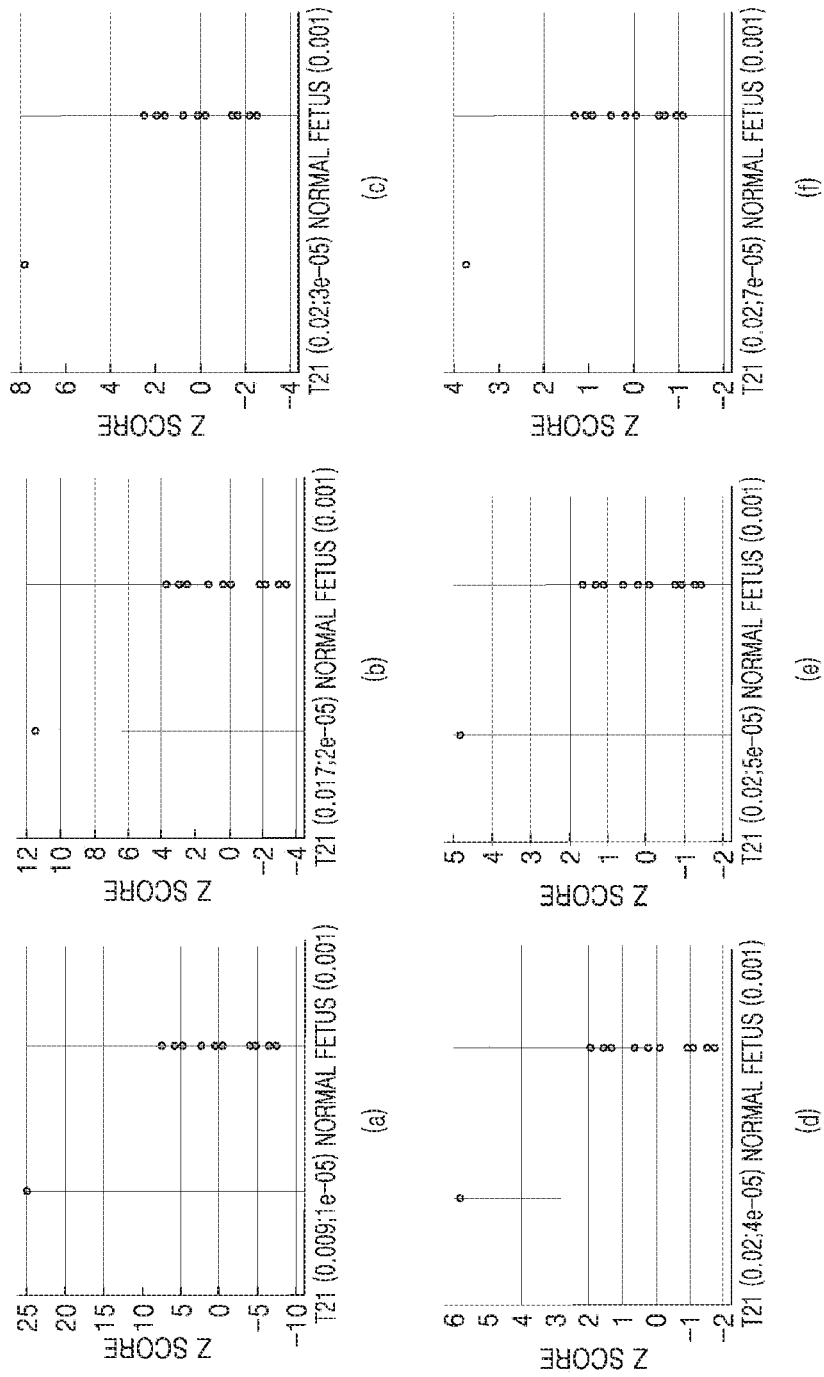
FIG. 5B shows results of calculating Z scores of T21 verification samples with a GC content of 0.43 and euploid verification samples using the euploid samples of sets A to F adaptively selected in FIG. 5A as reference samples.

(A) to (F) of FIG. 5B show results of calculating Z scores of T21 test samples and euploid test samples using the euploid samples of sets A to F adaptively selected in FIG. 5A as reference samples. In (A), the reference samples corresponding to set A were selected from a shared range of GC content 0.437±0.009 and Rf linear predicted value±1e-05. In this regard, the remaining test samples not selected as the representative test sample were used as verification samples. In (B) to (F), reference samples were selected in the same manner as in (A). z scores of the T21 test samples were calculated from the selected reference samples and test samples.

Further, euploid samples arbitrarily selected in the GC content range of 0.437±0.001 were used as test samples, and the 6 sets of the reference samples were used to calculate z scores of the euploid test samples. As shown in FIG. 5B, when the adaptively selected sets A to F were used, normal fetus (euploid) and T21 fetus were clearly distinguished, and a threshold which is the z score for T21 fetus was unambiguous.

(iv) Application of Adaptive Selection Method to T21 Samples in GC Content Region of 0.44

Figure 6A:
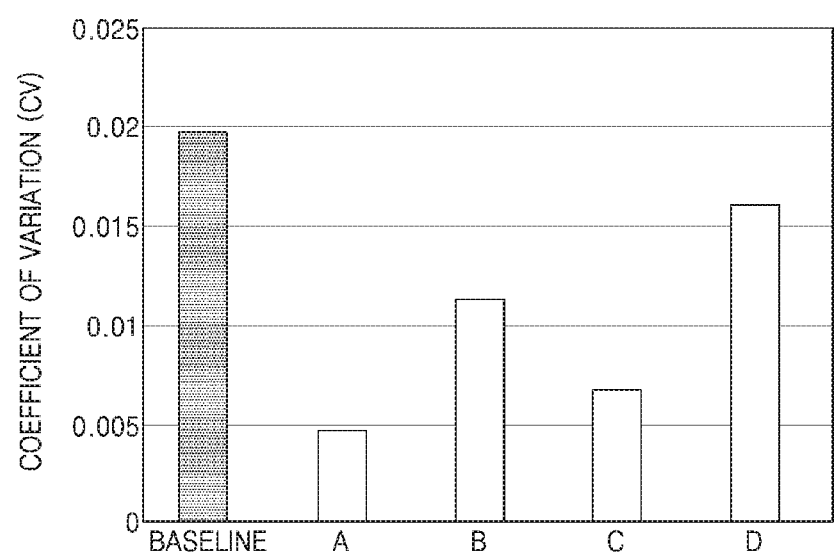
FIG. 6A shows coefficient of variation for four sets of reference samples which were selected according to a shared region of GC and Rf based on a representative sample of chromosome T21 with a GC content of 0.446.

Similarly, of the four test samples in the GC content region of 0.44 of chromosome 21, samples in the GC content region of 0.446 of chromosome T21 were selected as representative test samples, and other samples were used to demonstrate results using the adaptive reference samples. Four sets of reference samples (A, B, C, and D) were selected according to shared ranges of GC content and Rf based on the representative test samples (A: n=38, B: n=127, C: n=93, D: n=181), respectively. In FIG. 6A, CVs for the selected four sets of reference samples are shown.

Figure 6B:
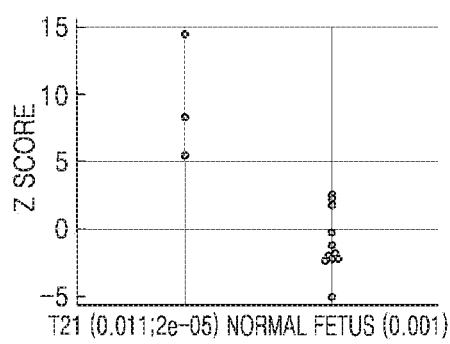
FIG. 6B shows results of calculating Z scores of T21 verification samples with a GC content of 0.44 and euploid verification samples using the euploid samples of sets A to D adaptively selected in FIG. 6A as reference samples.
Figure 6B:
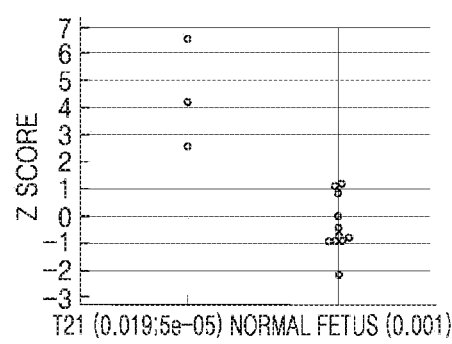
Figure 6B:
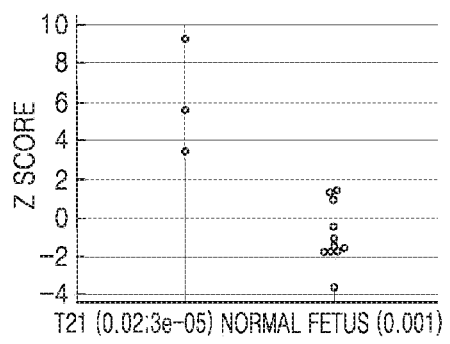
Figure 6B:
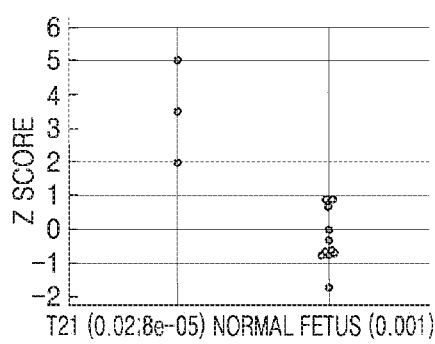

(A) to (D) of FIG. 6B show results of calculating Z scores of T21 test samples and euploid test samples using the euploid samples of sets A to D adaptively selected in FIG. 6A as reference samples. In (A), the reference samples corresponding to set A were selected from a shared range of GC content 0.446±0.011 and Rf linear predicted value±2e-05. In this regard, the remaining test samples not selected as the representative test sample were used as verification samples. In (B) to (D), reference samples were selected in the same manner as in (A). z scores of the T21 test samples were calculated from the selected reference samples and test samples. Further, euploid samples arbitrarily selected in the GC content range of 0.446±0.001 were used as test samples, and the 6 sets of the reference samples were used to calculate z scores of the euploid test samples. As shown in FIG. 6B, when the adaptively selected sets A to D were used, normal fetus (euploid) and T21 fetus were clearly distinguished, and a threshold which is the z score for T21 fetus was unambiguous.

(3) Detection of T18 Sample Using Adaptive Reference Sample

Trisomy 18 (T18) sample was detected by the adaptive selection method as described in 5.(2).

Figure 7A:
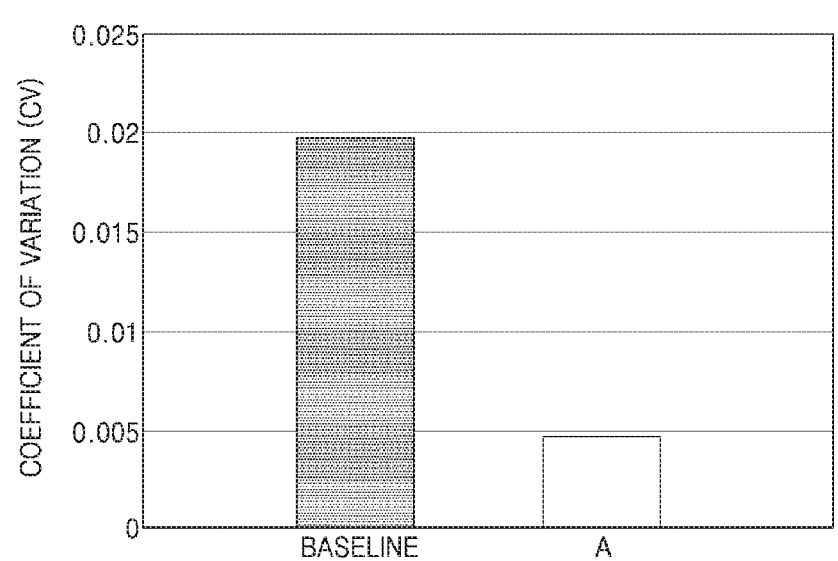
FIG. 7A shows coefficient of variation for sets of reference samples which were selected according to a shared region of GC and Rf based on a sample of chromosome T18 with a GC content of 0.45.
Figure 7B:
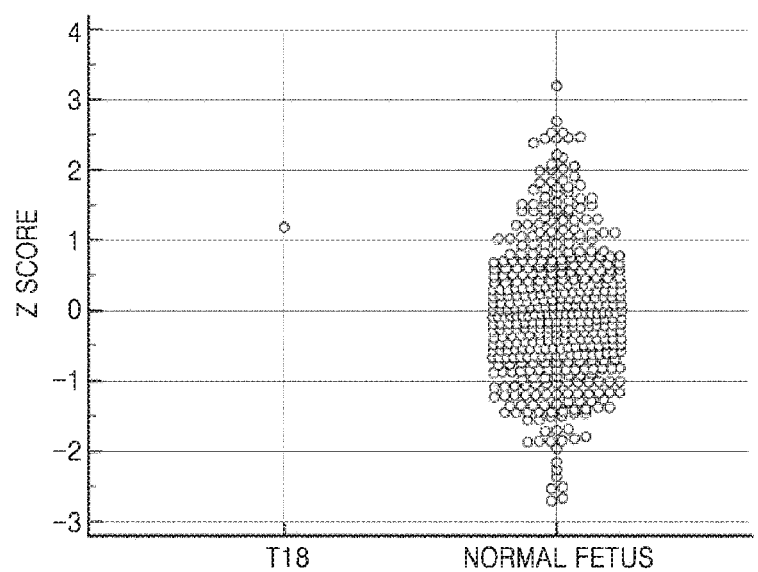
FIG. 7B shows z scores of all reference samples and a T18 sample with a GC content of 0.45.

Because there was only one T18 sample, a representative test sample was also used as a test sample. One set (A) of reference samples was selected according to a shared range of GC content and Rf based on the representative test sample (A: n=8). In FIG. 7A, CVs for the set A and reference value (non-selected reference sample) are shown. FIG. 7B shows Z scores of non-selected reference sample and T18 sample.

Figure 7C:
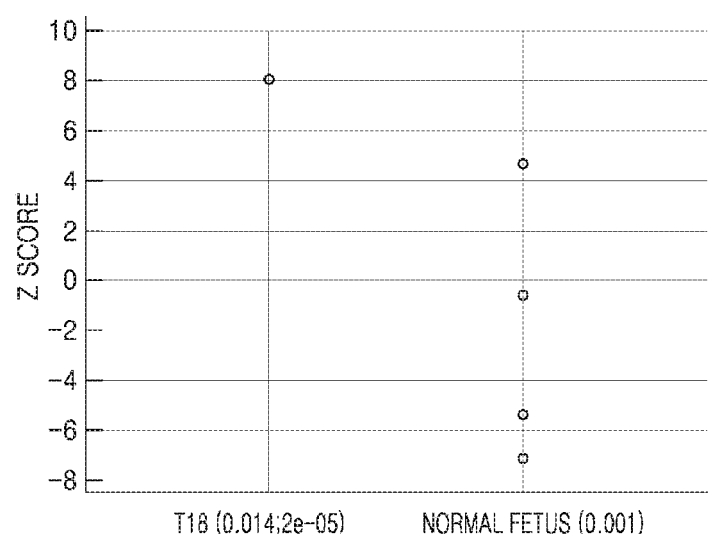
FIG. 7C shows results of calculating Z scores of T18 test samples with a GC content of 0.45 and euploid test samples using the euploid samples adaptively selected as reference samples.

In FIG. 7C, the reference sample corresponding to set A were selected from a shared range of GC content 0.45±0.014 and Rf linear predicted value±2e-05. Further, euploid samples arbitrarily selected in the GC content range of 0.45±0.001 were used as test samples, and the reference sample set was used to calculate z scores of the euploid test samples.

As shown in FIGS. 7B and 7C, when the non-selected reference sample was used, normal fetus (euploid) and T18 fetus were not distinguished. In contrast, when the adaptively selected set A was used, normal fetus (euploid) and T18 fetus were clearly distinguished.

(4) Detection of T13 Sample Using Adaptive Reference Sample

Trisomy 13 (T13) sample was detected by the adaptive selection method as described in 5.(2).

Figure 8A:
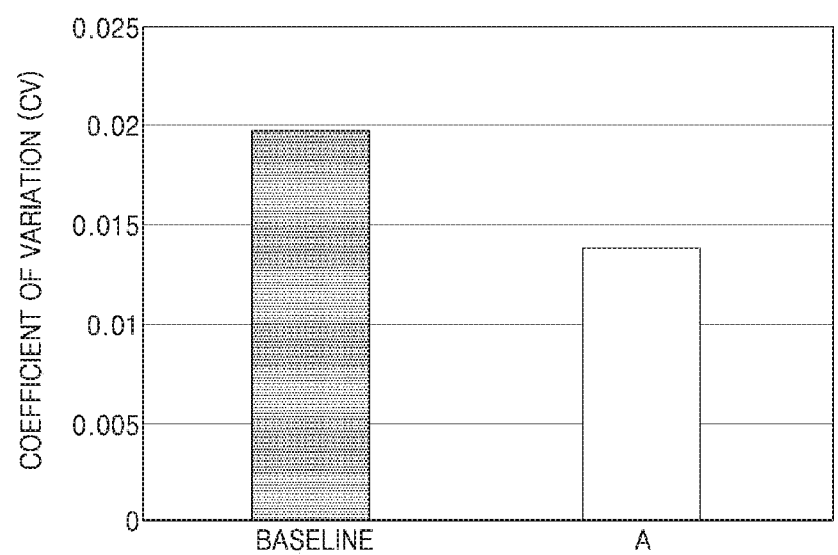
FIG. 8A shows coefficient of variation for sets of reference samples which were selected according to a shared region of GC and Rf based on a sample of chromosome T13 with a GC content of 0.421.
Figure 8B:
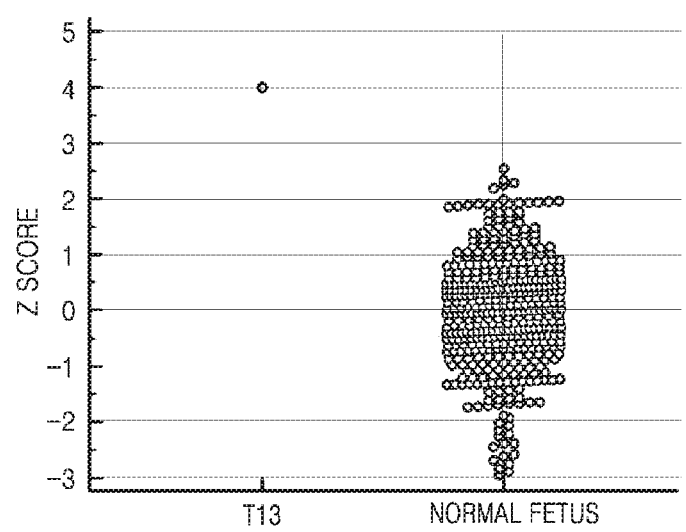
FIG. 8B shows z scores of all reference samples and a T13 sample with a GC content of 0.421.

Because there was only one T13 sample, a representative test sample was also used as a test sample. One set (A) of reference samples was selected according to a shared range of GC content and Rf based on the representative test sample (A: n=177). In FIG. 8A, CVs for the set A and reference value (non-selected reference sample) are shown. FIG. 8B shows Z scores of non-selected reference sample and T13 sample.

Figure 8C:
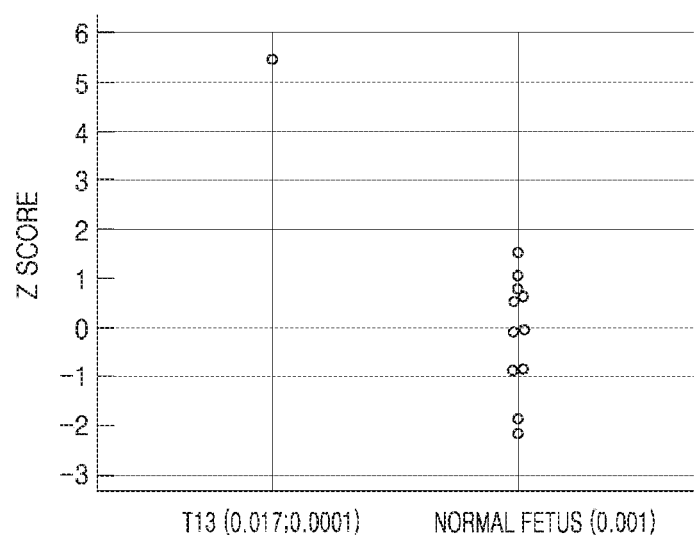
FIG. 8C shows results of calculating Z scores of T13 test samples with a GC content of 0.421 and euploid test samples using the euploid samples adaptively selected as reference samples.

In FIG. 8C, the reference sample corresponding to set A were selected from a shared range of GC content 0.421±0.017 and Rf linear predicted value±0.0001. Further, euploid samples arbitrarily selected in the GC content range of 0.421±0.001 were used as test samples, and the reference sample set was used to calculate z scores of the euploid test samples.

As shown in FIGS. 8B and 8C, when the non-selected reference sample was used, normal fetus (euploid) and T13 fetus were distinguished (z score difference of about 1.5), but when the adaptively selected set A was used, normal fetus (euploid) and T13 fetus were more clearly distinguished (z score difference of about 4).

(5) Relationship of Fraction of Reads and GC Content in Chromosomes

Figure 9A:
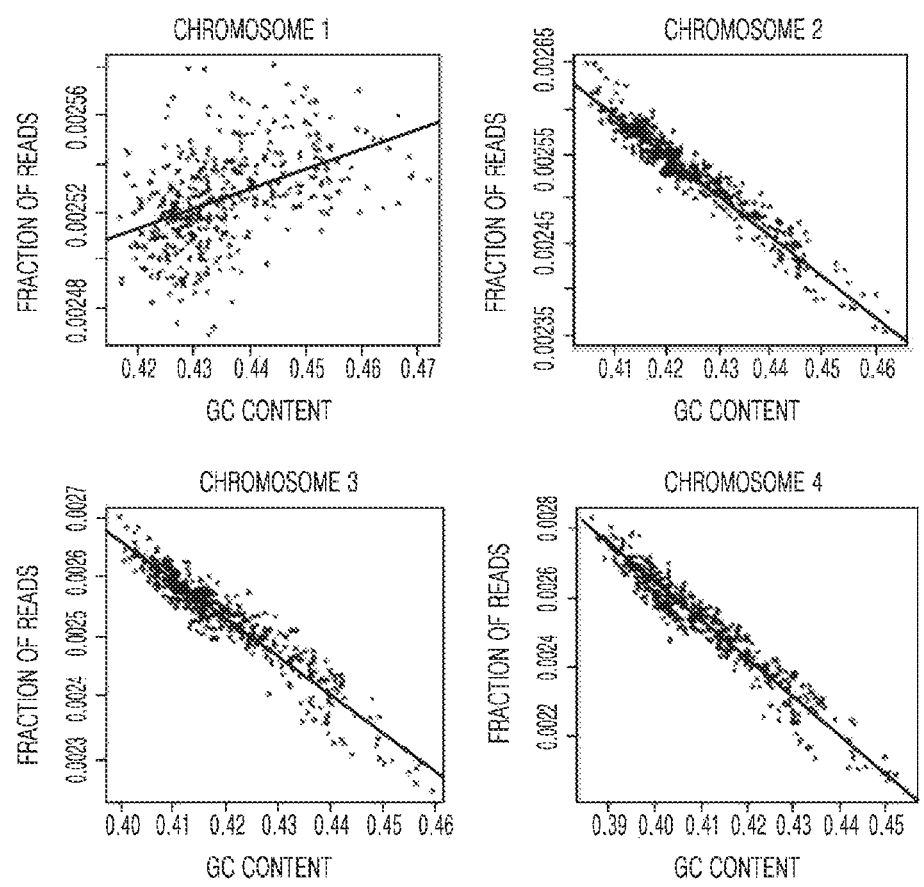
FIGS. 9A to 9F show the relationship between Rfs of chromosomes 1 to 22 and GC contents of euploid reference samples (n=396) as confirmed by karyotyping.
Figure 9B:
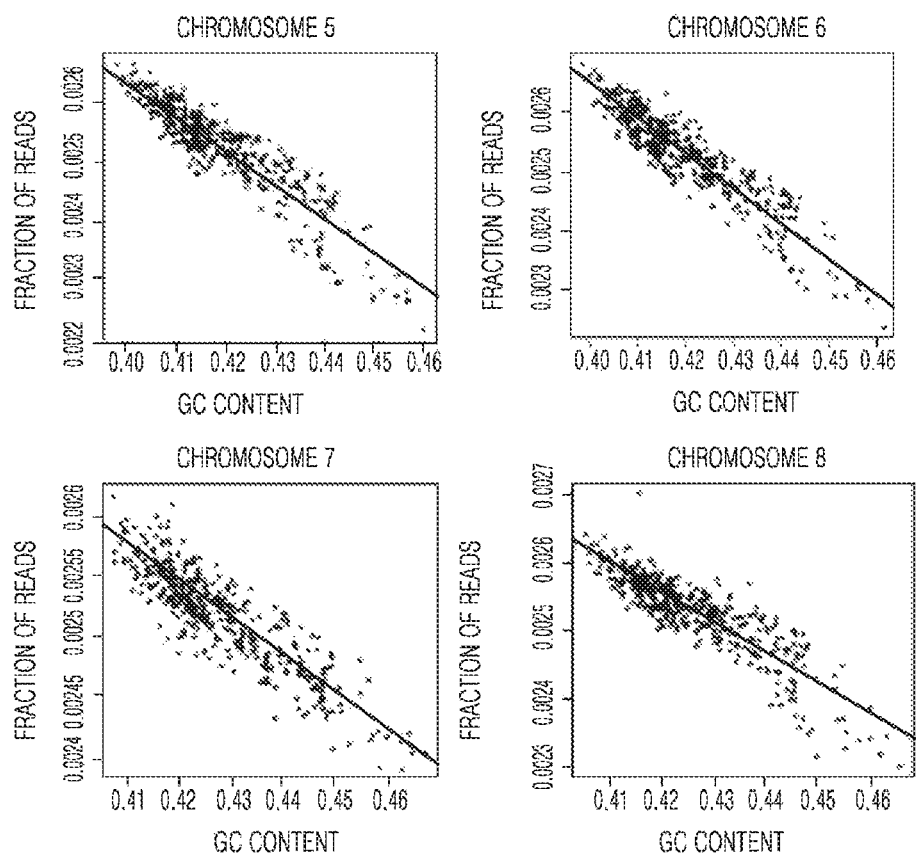
Figure 9C:
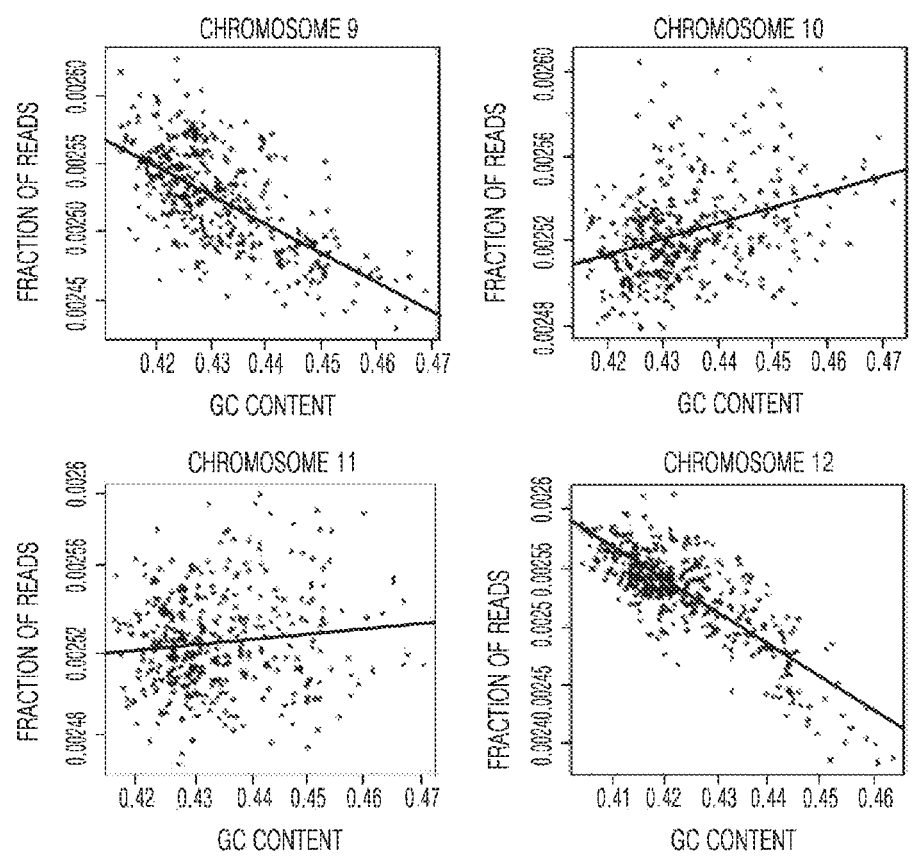
Figure 9D:
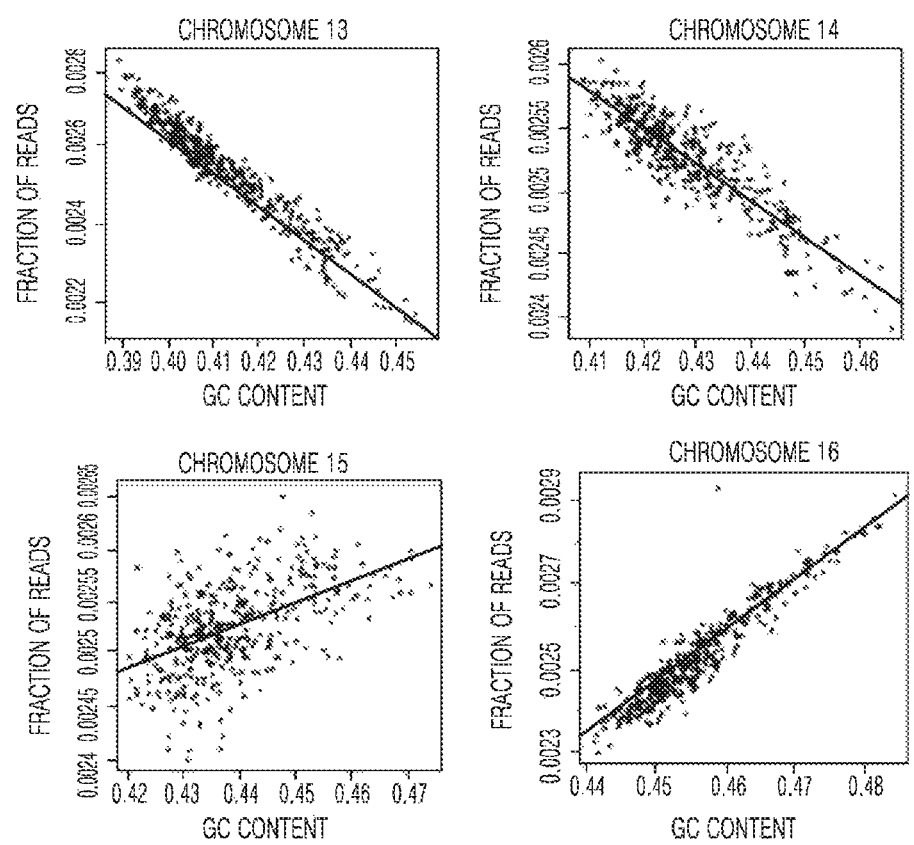
Figure 9E:
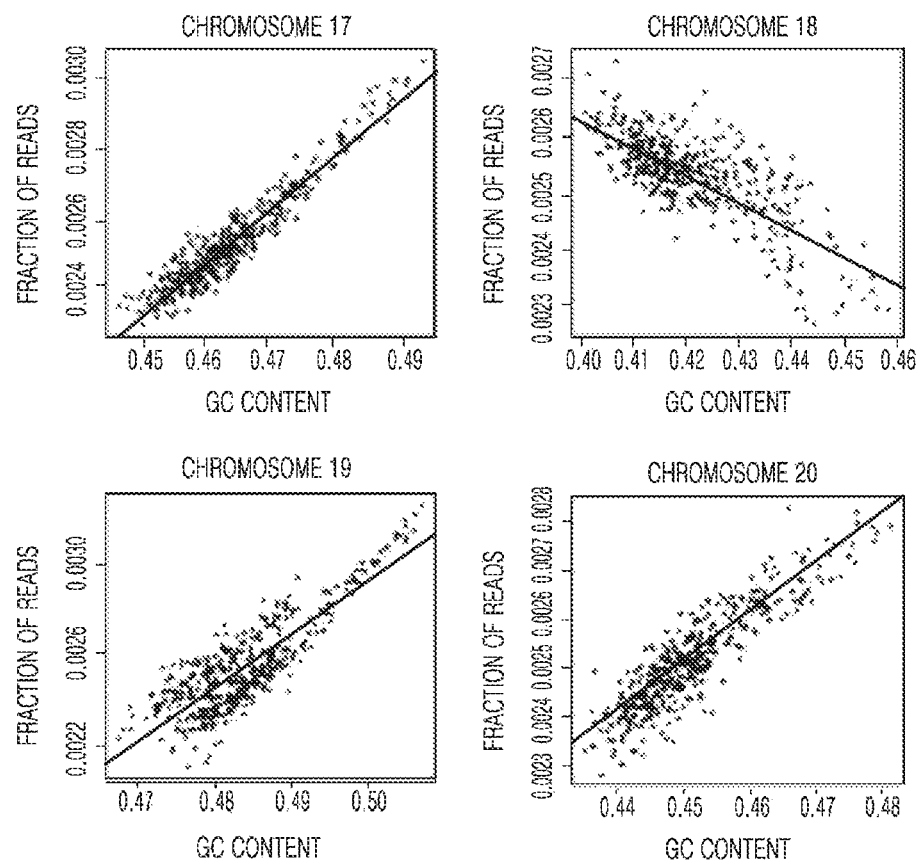
Figure 9F:
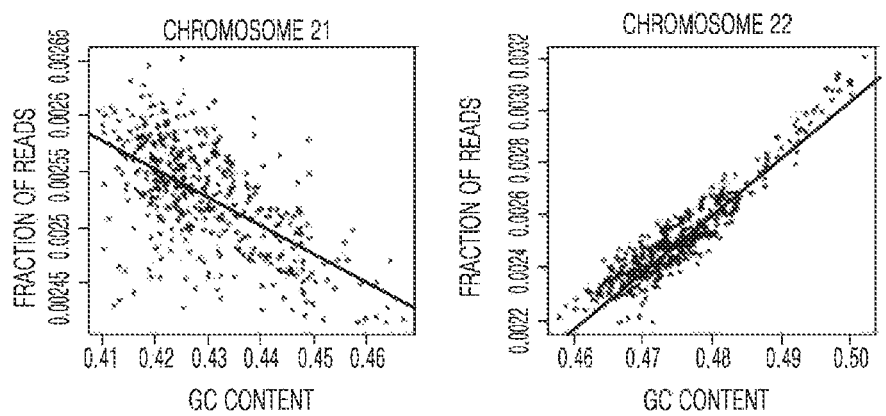

The relationship of a fraction of reads and a GC content in respective chromosomes was calculated by fitting to a linear model, and results are shown in FIGS. 9A and 9F. FIGS. 9A to 9F show the relationship between Rfs of chromosomes 1 to 22 and GC contents of the euploid controls (n=396) as confirmed by karyotyping.

As shown in FIGS. 9A to 9F, there was a linear relationship between Rf of chromosome and GC content. Therefore, in order to detect trisomy samples, reference samples belonging to a range set based on Rf of test chromosome and GC content may be selected from a target chromosome.

Accordingly, whether a test sample is a trisomy fetus or not may be detected with excellent sensitivity and specificity by comparing Z scores calculated from selected reference samples and Z score calculated from the test sample.

The invention claimed is:

1. A method of detecting chromosomal aneuploidy of a target fetal chromosome in a test sample using a massively parallel sequencing system, the method comprising:
    isolating a plurality of nucleic acid fragments from a biological sample of a pregnant woman including fetal nucleic acid fragments as the test sample;
    obtaining sequence information (reads) of the plurality of nucleic acid fragments by performing massively parallel sequencing of the plurality of nucleic acid fragments using a massively parallel sequencing system;
    mapping the reads obtained using the massively parallel sequencing system to a reference human genome to assign the reads of the plurality of the nucleic acid fragments to the target fetal chromosome;
    calculating a GC content and a fraction of reads (Rf) of the plurality of the nucleic acid fragments on the target fetal chromosome to the number of the nucleic acid fragments, based on the reads of the plurality of the nucleic acid fragments assigned to the chromosome;
    selecting adaptive reference samples belonging to a shared range of unit values of Rf and unit values of GC content from reference samples, based on the calculated Rf and GC content on the target chromosome;
    calculating z scores of verification reference samples and a z score of the test sample using the selected adaptive reference samples;
    determining that the target chromosome has chromosomal aneuploidy when, by comparing the calculated z scores of the verification reference samples with the z score of the test sample, the z score of the test sample is larger than the z scores of the verification reference samples; and
    performing an invasive method selected from chorionic villus sampling, amniocentesis, and sampling from an umbilical cord, based on the determining that the target chromosome has chromosomal aneuploidy,
    wherein the selected adaptive reference samples have a lower coefficient of variance than reference samples without adaptive selection.

2. The method of claim 1, wherein the biological sample is blood, plasma, serum, urine, saliva, mucus, sputum, feces, tears, or a combination thereof.

3. The method of claim 1, further comprising excluding intervals with a low confidence level for reads from subjects of analysis by examining depth distribution of the reads of the nucleic acid fragments assigned to the chromosome at each interval, after assigning the reads of the nucleic acid fragments to the chromosome.

4. The method of claim 3, wherein the interval is an interval set in units of about 5 kb to about 50 kb.

5. The method of claim 3, wherein the excluding of intervals with a low confidence level for the reads from subjects of analysis comprises removing mismatches, removing multi-mapped reads, removing duplicated reads, or a combination thereof.

6. The method of claim 1, further comprising performing locally weighted scatterplot smoothing (LOWESS or LOESS) regression analysis of the reads of the nucleic acid fragments according to the following Equation 1 to reduce GC content bias, after assigning the reads of the nucleic acid fragments to the chromosome:

$$Rf_{ij}' = RC_{ij} / \Sigma_{j=1}^{22} RC_{ij} \qquad \text{(Equation 1)}$$

wherein $Rf_{ij}'$ represents a corrected fraction of reads on chromosome j in sample i, and $RC_{ij}$ represents a corrected number of unique reads on chromosome j in sample i.

7. The method of claim 1, further comprising performing normalization of the reads of the nucleic acid fragments according to the following Equation 2, after assigning the reads of the nucleic acid fragments to the chromosome:

$$Rf_{i'j'} = Rf_{ij'} / \Sigma_{i=1}^{N} Rf_{ij'} \qquad \text{(Equation 2)}$$

wherein $Rf_{i'j'}$ represents a normalized fraction of reads on chromosome j in sample i, and N represents the total number of samples.

8. The method of claim 1, wherein the reference sample are obtained from a biological sample of a pregnant woman carrying a euploid fetus.

9. The method of claim 1, further comprising establishing a linear regression model from all of the reference samples.

10. The method of claim 1, further comprising extending the unit values of Rf of the reference samples according to Rf values of the test samples, extending the unit values of GC of the reference samples according to GC contents of the test samples, or a combination thereof.

11. The method of claim 1, wherein the calculating of z scores of the verification reference samples and z scores of the test samples comprises performing a linear regression analysis according to the following Equation 3 and calculating a linear predicted value of Rf according to the following Equation 4:

$$Rf_{ij'} = \alpha + \beta \times GC_{ij'} + e \quad \text{(Equation 3)}$$

Wherein, in Equation 3, Rfi'j' represents a normalized fraction of reads on chromosome j in sample i, α represents a constant, β represents a coefficient factor between GC content and Rf, and e represents a residual (R); and $$Rf'_{ij'} = \alpha + \beta \times GC_{ij'} \quad \text{(Equation 4)}$$

in Equation 4, Rfi'j' represents a fitted predicted value of a fraction of reads on chromosome j in sample i, α represents a constant, and β represents a coefficient factor between GC content and Rf.

12. The method of claim 11, wherein the calculating of z scores of the verification reference samples and z scores of the test samples comprises calculating a residual (R) from a calculated value from the linear regression analysis and the calculated linear predicted value according to the following Equation 5, and calculating a Z score from the calculated residual according to the following Equation 6:

$$R = Rf_{ij'} - Rf'_{ij'} \quad \text{(Equation 5); and}$$

$$z\ score = (R - R')/\sigma' \quad \text{(Equation 6)}$$

wherein, in Equation 6, R' represents a mean value of a residual of an adaptive reference sample, R represents a residual value of a test sample, and a' represents a standard deviation of the residual of the adaptive reference sample.

13. The method of claim 1, further comprising
selecting reference samples belonging to GC content±unit value of the target chromosome or GC content±unit value of the adaptive reference samples, as verification samples;
calculating z scores of the verification samples; and
verifying that the target chromosome has chromosomal aneuploidy by comparing the calculated z scores of the verification samples with the z scores of the test samples.

14. The method of claim 1, wherein the target chromosome is chromosome 13, chromosome 18, chromosome 21, an X chromosome, a Y chromosome, or a combination thereof.

15. The method of claim 1, wherein the chromosomal aneuploidy is trisomy 13, trisomy 18, trisomy 21, XO, XXX, XXY, XYY, or a combination thereof.

16. A system containing a computer-readable medium having recorded thereon a program that performs the steps of:

mapping reads obtained from massively parallel sequencing of a plurality of nucleic acid fragments isolated from a biological sample of a pregnant woman including fetal nucleic acid fragments as a test sample to a reference human genome to assign the reads of the plurality of the nucleic acid fragments to a target chromosome, wherein the massively parallel sequencing was performed using a massively parallel sequencing system;

calculating a GC content and a fraction of reads (Rf) of the plurality of the nucleic acid fragments on the target chromosome to the number of the nucleic acid fragments, based on the reads of the plurality of the nucleic acid fragments assigned to the chromosome;

selecting adaptive reference samples belonging to a shared range of unit values of Rf and unit values of GC content from reference samples, based on the calculated Rf and GC content on the target chromosome;

calculating z scores of verification reference samples and a z score of the test sample using the selected adaptive reference samples; and determining that the target chromosome has chromosomal aneuploidy when, by comparing the calculated z scores of the verification reference samples with the z score of the test sample, the z score of the test sample is larger than the z scores of the verification reference samples;

wherein the selected adaptive reference samples have a lower coefficient of variance than reference samples without adaptive selection; and wherein the result obtained by determining that the target chromosome has chromosomal aneuploidy is used to avoid performing an invasive method selected from chorionic villus sampling, amniocentesis, and sampling from an umbilical cord, based on the determining that the target chromosome has chromosomal aneuploidy.

\* \* \* \* \*